United States Patent [19]

Miyashita et al.

[11] 4,264,596
[45] Apr. 28, 1981

[54] MAYTANSINOIDS, PHARMACEUTICAL COMPOSITIONS THEREOF AND METHOD OF USE THEREOF

[75] Inventors: Osamu Miyashita, Osaka; Hiroshi Akimoto, Nishinomiya, both of Japan

[73] Assignee: Takeda Chemical Industries, Ltd., Osaka, Japan

[21] Appl. No.: 171,460

[22] Filed: Jul. 23, 1980

[51] Int. Cl.$^3$ .................... A61K 31/395; C07D 498/18
[52] U.S. Cl. .......................... 424/248.54; 260/239.3 P
[58] Field of Search ................................. 260/239.3 P; 424/248.54

[56] References Cited

U.S. PATENT DOCUMENTS

| | | | |
|---|---|---|---|
| 3,896,111 | 7/1975 | Kupchan et al. | 260/239.3 P |
| 4,137,230 | 1/1979 | Hashimoto et al. | 260/239.3 P |
| 4,162,940 | 7/1969 | Higashide et al. | 260/239.3 P |
| 4,190,580 | 2/1980 | Hashimoto et al. | 260/239.3 P |

OTHER PUBLICATIONS

Higashide et al., "Nature", vol. 270, 22/29, Dec. 1977, pp. 721–722.

Kupchan et al., "Journal of Medicinal Chemistry", 1978, vol. 21, No. 1, pp. 31–37.

*Primary Examiner*—Robert T. Bond
*Attorney, Agent, or Firm*—Wegner & Bretschneider

[57] ABSTRACT

Novel maytansinoid compounds of the formula:

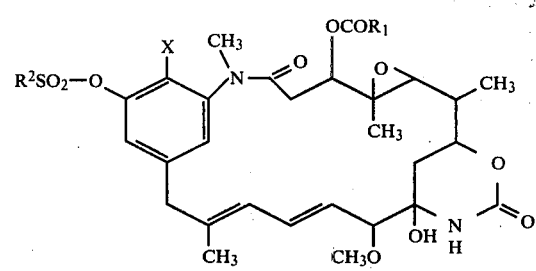

wherein X is H or Cl, $R^1$ is an alkyl group of 2 to 4 carbon atoms and $R^2$ is a lower alkyl group or an unsubstituted or substituted phenyl or aralkyl group, have antimitotic, antitumor and antimicrobial activities.

13 Claims, No Drawings

MAYTANSINOIDS, PHARMACEUTICAL COMPOSITIONS THEREOF AND METHOD OF USE THEREOF

This invention relates to novel maytansinoid compounds which are of value as medicines, and to their production and use.

More particularly, this invention relates to maytansinoid compounds of the formula:

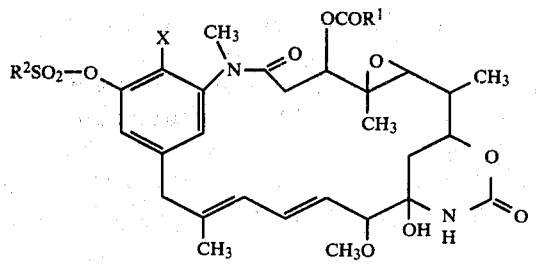

wherein X is H or Cl, $R^1$ is an alkyl group of 2 to 4 carbon atoms and $R^2$ is a lower alkyl group or an unsubstituted or a substituted phenyl or aralkyl group, and their production and use.

Referring to the above formula (I), the $C_{2-4}$ alkyl group $R^1$ is exemplified by ethyl, propyl, isopropyl, butyl, sec-butyl, tert-butyl, etc. Especially preferred is isopropyl.

The lower alkyl group $R^2$ includes, for example, alkyl groups of about 1 to 4 carbon atoms (e.g. methyl, ethyl, propyl, isopropyl, butyl, isobutyl, sec-butyl, tert-butyl).

The aralkyl group $R^2$ includes, for example, phenyl-$C_{1-3}$ alkyl groups (e.g. benzyl, phenethyl, α-methylbenzyl).

The said phenyl and aralkyl groups $R^2$ may be substituted. The substituents include, for example, $C_{1-4}$ alkyl groups (e.g. methyl, ethyl, propyl, isopropyl, butyl, isobutyl, sec-butyl, tert-butyl), $C_{1-4}$ alkoxy groups (e.g. methoxy, ethoxy, propoxy, isopropoxy, butoxy), nitro, amino, mono- or di-$C_{1-4}$ alkylamino (e.g. methylamino, ethylamino, dimethylamino, diethylamino), mono- or di-$C_{1-4}$ alkanoylamino (e.g. formylamino, acetylamino, propionylamino, butyrylamino), halogenated mono- or di-$C_{1-4}$ alkanoylamino (e.g. trifluoroacetylamino, chloroacetylamino, dichloroacetylamino), halogens (e.g. fluorine, chlorine, bromine, iodine), halogenated $C_{1-4}$ alkyl (e.g. trifluoromethyl), etc.

A preferred embodiment provides maytansinoid compounds of formula (I) wherein X is H or Cl, $R^1$ is $C_{2-4}$ alkyl and $R^2$ is $C_{1-4}$ alkyl, phenyl or phenyl-$C_{1-3}$ alkyl, said phenyl or phenyl-$C_{1-3}$ alkyl being unsubstituted or substituted by $C_{1-4}$ alkyl, $C_{1-4}$ alkoxy, nitro, amino, mono- or di-$C_{1-4}$ alkylamino, mono- or di-$C_{1-4}$ alkanoylamino, halogenated mono- or di-$C_{1-4}$ alkanoylamino, halogen or halogenated $C_{1-4}$ alkyl.

Referring to $R^2$, preferred species will be shown below as the group of $R^2SO_2$—. Thus, they include methanesulfonyl, ethanesulfonyl, 2-propanesulfonyl, 2-butanesulfonyl, butanesulfonyl, α-toluenesulfonyl (benzylsulfonyl), β-ethylbenzenesulfonyl, α-phenylpropanesulfonyl, benzenesulfonyl, p-toluenesulfonyl, p-chlorobenzenesulfonyl, o-, m- or p-nitrobenzenesulfonyl, p-methoxybenzenesulfonyl, p-acetamidobenzenesulfonyl, p-trifluoroacetamidobenzenesulfonyl, p-aminobenzenesulfonyl, p-methylaminobenzenesulfonyl, p-dimethylaminobenzenesulfonyl, etc.

The compound of formula (I) can be produced for example by reacting a 20-demethoxy-20-hydroxymaytansinol 3-lower carboxylate of the formula:

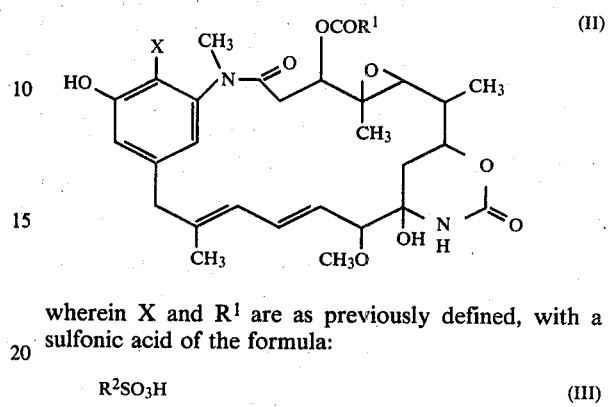

wherein X and $R^1$ are as previously defined, with a sulfonic acid of the formula:

$$R^2SO_3H \qquad (III)$$

wherein $R^2$ is as previously defined, or a reactive derivative thereof (e.g. halide, azolide, acid anhydride, etc.)

The reaction is normally carried out in the presence of a base. The base is exemplified by alkali metal hydroxides (e.g. sodium hydroxide, potassium hydroxide), alkali metal carbonates (e.g. sodium carbonate, potassium carbonate), tertiary amines (e.g. triethylamine, pyridine, α-, β- or γ-picoline, 2,6-lutidine, 4-dimethylaminopyridine, 4-pyrrolidinopyridine, dimethylaniline, diethylaniline), imidazole, 2-methylimidazole, triazole, etc. Such a base is normally used in a proportion of 1 to 20 molar equivalents based on the starting compound (II) and when a tertiary amine which is liquid at room temperature is employed as the base (e.g. triethylamine, pyridine), it may be used also as the reaction solvent.

The reaction is preferably carried out in a solvent. The solvent includes, in addition to the above-mentioned tertiary amine, such solvents as esters (e.g. ethyl acetate), ethers (e.g. diethyl ether, dioxane, tetrahydrofuran), halogenated hydrocarbons (e.g. dichloromethane, chloroform), nitriles (e.g. acetonitrile, propionitrile), aromatic hydrocarbons (e.g. benzene, toluene), dimethylformamide, dimethyl sulfoxide, sulfolane, etc. or a suitable mixture of such solvents.

In some instances the reaction is preferably conducted in a two phase system of aqueous and organic phases by a procedure which is known as the Schotten-Bauman reaction and in such cases it is sometimes more desirable to conduct the reaction in the presence of a phase transfer catalyst (e.g. tetraethylammonium hydroxide, benzyltrimethylammonium bromide, benzyltriethylammonium iodide, cetyltrimethylammonium chloride or bromide). The preferred organic solvent as the organic phase for the reaction is exemplified by halogenated hydrocarbons, aromatic hydrocarbons, etc., while an aqueous solution of alkali metal hydroxide is preferably used as the aqueous phase.

The amount of said reactive derivative of sulfonic acid (III) as said sulfonating agent is about 1 to 20 molar equivalents, preferably about 3 to 15 equivalents based on the starting compound (II).

It may also be so arranged that said reactive derivative is formed in situ, i.e. by the reaction of sulfonic acid (III) with an inorganic halogenating agent (e.g. thionyl chloride), a carbodiimide (e.g. N,N'-dicyclohexylcarbodiimide, N-cyclohexyl-N'-(2-morpholino)ethylcarbodiimide), carbonyldiimidazole or the like within the reaction medium or in the same vessel.

When the desired product is a compound having, in the moiety which comes of the sulfonylating agent, such a group (e.g. OH, $NH_2$) liable to be sulfonylated, one may take the procedure of preparing a compound having such a group protected in the conventional manner and, then, subjecting the compound to deprotection.

The protective groups which can be utilized include, for example, lower ($C_{1-4}$) alkanoyl (e.g. formyl, acetyl), lower ($C_{2-5}$)alkoxycarbonyl, (e.g. methoxycarbonyl, tert-butoxycarbonyl), benzyloxycarbonyl, halogenated lower ($C_{1-4}$)alkanoyl (e.g. trifluoroacetyl, chloroacetyl), etc.

Removal of such protective groups can be accomplished by methods known per se (e.g. reduction, acid decomposition, hydrolysis).

The maytansinoid compound (I) produced in the described manner can be isolated and recovered from the reaction mixture by conventional procedures, e.g. concentration, solvent extraction, chromatography, recrystallization, etc.

The maytansinoid compound (I) according to this invention has potent antimitotic activity and antitumor activity with comparatively low toxicity, and when administered to tumor-bearing animals [e.g. leukemia (P-388, mouse), melanoma (B-16, mouse)], inhibits the growth of tumor cells and produces a marked increase of survival time. Therefore, the compound (I) can be used as an effective antitumor drug for warm-blooded animals (e.g. mouse, rat, rabbit, dog, cat, man). The compound (I) is safely administered orally or parenterally as a suitable pharmaceutical composition (e.g. injection) as formulated with a per se known carrier, diluent or the like. When the compound (I) is administered by injection, subcutaneous, intraperitoneal, intravenous, intramuscular or other suitable route may be selected. In case of intravenous administration for prolonging life span of the animal suffering from, for example, leukemia or melanoma, the dosage may be decided from the range of about 1 to 500 μg/kg body weight per injection, preferably 5 to 100 μg/kg body weight, with reference to the condition, animal species and other factors.

An injection may be prepared in the established manner, for example by dissolving about 50 μg to 3 mg of compound (I) in about 0.5 ml of alcohol (e.g. ethanol) and making it up to 10 ml with physiological saline. When a small dosage is indicated, the above solution may be further diluted with physiological saline.

The maytansinoid compound (I) of this invention is useful in that it displays antimicrobial activity, e.g. antifungal and antiprotozoal activities. Thus, for example, the maytansinoid compounds (I) are useful for treating *Tetrahymena pyriformis* W. As an antifungal or/and antiprotozoal agent, compound (I) can be advantageously used for the investigation of bacterial flora in soils, active sludge, animal body fluids, etc. Thus, in separating useful bacteria from soil samples or in studying the action of bacteria to the exclusion of protozoa and fungi in connection with the operation and analysis of active sludge systems for waste water treatment, it is possible to ensure a selective growth of bacterial flora, without permitting growth of the concomitant fungi and protozoa. More specifically, a test sample is added to a liquid or solid medium and 0.1 ml of a 1% methanol-water solution of about 10 to 100 μg/ml of compound (I) is added to the medium, followed by incubation.

The maytansinoid compound (I), in an amount of 0.02 ml of a 1 mg/ml aqueous solution, inhibits growth of, for example, the causative microorganisms of stem rot, Helminthosporium leaf spot and sheath blight in rice plants and, therefore, can be used in the control of such plant diseases by spraying rice plants with a solution of compound (I) in 1% methanol-water, the concentration of which may range from about 0.5 to 5 μg/ml.

The starting compound (II) used for the production of the contemplated compound of this invention can be produced for example in accordance with the description in the specification of Japanese Patent Application No. 160787/1978 (U.S. patent application Ser. No. 19,612; European Patent Publication No. 4466), i.e. by contacting a maytansinoid compound of the formula:

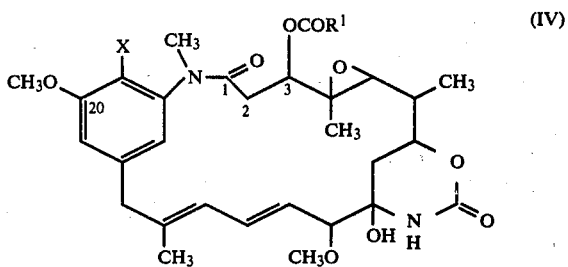

(IV)

wherein X and $R^1$ are as previously defined, with a culture broth, inclusive of processed matters derived therefrom, of a microorganism belonging to the genus Bacillus, the genus Streptomyces or the genus Actinomyces which is capable of transforming the 20-methoxy group of (IV) into a hydroxyl group.

The microorganisms thus useful for the method of transforming the 20-methoxy group into a hydroxyl group include strains of the genera Bacillus, Streptomyces and Actinomyces, and their mutants, which are capable of transforming the methoxy group in 20-position of maytansinoid compound (IV) into a hydroxyl group. Among the microorganisms useful for the purpose are *Bacillus megaterium* IFO 12108, *Streptomyces flavotricini* IFO 12770, *Streptomyces platensis* IFO 12901, *Streptomyces libani* IFO 13452 and *Actinomyces nigrescens* IFO 12894. The microorganisms given IFO numbers above have been listed on the List of Cultures, 1978 (Sixth Edition), published by Institute for Fermentation, Osaka. The microorganisms listed there are available from the same Institute.

The compound of the above formula (IV) in which X is a hydrogen atom, i.e. dechloromaytansinoid compound, can be produced for example in accordance with the description in the specification of Japanese Patent Application No. 139995/1978 (U.S. patent application Ser. No. 92,954; European Patent Publication No. 11277), i.e. by acylating dechloromaytansinol of the formula:

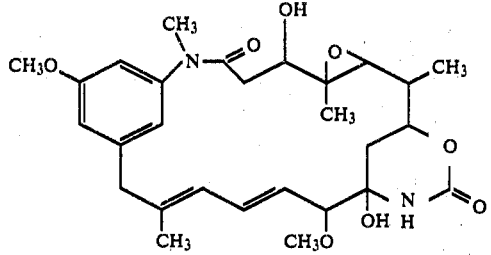

with a carboxylic acid of the formula:

$$R^1\text{—COOH} \qquad (VI)$$

wherein $R^1$ is as previously defined, or a reactive derivative thereof. The dechloromaytansinol (V) can be produced by reducing a compound (IV) in which X is Cl with a metal hydride (e.g. lithium aluminum hydride).

This invention will hereinafter as described in further detail by way of reference and working examples which, however, are merely illustrative and not limitative of the invention. In the reference and working examples, Rf values are those found on silical gel TLC (Merck, HPTLC) unless otherwise indicated. Further, Ansamitocin P-2, P-3 and P-4 mean the compounds (IV) in which X is Cl and $R^1$ means ethyl, isopropyl and isobutyl, respectively. PDM-3 is a compound (II) in which X is Cl and $R^1$ is isopropyl, i.e. 20-demethoxy-20-hydroxymaytansinol 3-isobutyrate. Dechloro-PDM-3 means a compound (II) in which X is H and $R^1$ is isopropyl, i.e. 19-dechloro-20-demethoxy-20-hydroxymaytansinol 3-isobutyrate.

REFERENCE EXAMPLE 1

In 800 ml of anhydrous tetrahydrofuran (THF) is dissolved 15.0 g of antibiotic Ansamitocin mixture (12% of Ansamitocin P-2, 71% of P-3 and 17% of P-4) and, under dry nitrogen gas streams, the solution is cooled to −50° C. in a dry ice-ethanol bath. Then, 13.0 g of lithium aluminum hydride (LAH) is added at one stroke and the mixture is stirred at a temperature from −50° C. to −22° C. for 2 hours. Then, at −28° C., a further 3 g of LAH is added and the reaction mixture is stirred at −28° C. to −22° C. for 80 minutes. Thereafter, at −50° C., 750 ml of 2 N HCl is added dropwise with caution and the reaction mixture is extracted three times with 2.6 l, 1.6 l and 0.8 l portions of ethyl acetate. The extracts are pooled, washed twice with a 100 ml each portion of saturated aqueous solution of sodium chloride and dried (MgSO$_4$, 250 g). The solvent is distilled off under reduced pressure and the residue (13.6 g) is chromatographed on a column of silica gel (1.2 kg), elution being carried out with ethyl acetate-water (98.5:1.5, V/V). The eluate is collected in 400-gram fractions. Fractions 35 through 52 are pooled, the solvent distilled off and the residue dried in vacuo to obtain 7.25 g of maytansinol. Then, fractions 53 through 68 are similarly treated to obtain 1.55 g of a substantially equimolar mixture of maytansinol and dechloromaytansinol. Similarly, fractions 69 through 86 yield 0.78 g of dechloromaytansinol.

This product is reprecipitated from chloroformhexane to obtain 0.71 g of dechloromaytansinol. m.p. 174°-179° C. (decompn.)

Mass spectrum (m/e): 469, etc.

UV spectrum ($\lambda_{max}^{MeOH}$) nm: 231.5, 241.5, 250.5, 277.5, 286

REFERENCE EXAMPLE 2

In 10 ml of anhydrous dichloromethane is dissolved 90 mg (0.170 mmol) of dechloromaytansinol followed by addition of 280 mg (1,772 mmols) of isobutyric anhydride and 44 mg (0.361 mmol) of 4-dimethylaminopyridine (DMAP). The mixture is stirred at room temperature for 1.5 hours, after which 22 mg (0.180 mmol) of DMAP is further added. The mixture is stirred at the same temperature for 17 hours. The reaction mixture is washed with 0.5 N-HCl (10 ml×2), aqueous sodium hydrogen carbonate (10 ml) and water (10 ml×2), and after drying, the solvent is distilled off. The residue (174 mg) is dissolved in chloroform, the solution is chromatographed on a silica gel column (20 mm out.-dia.×400 mm) and elution is carried out with chloroform-ethanol (from 100/1 to 40/1), the eluate being collected in 25-g fractions. Fractions 42 through 65 are pooled and the solvent is distilled off, whereby 69 mg of dechloromaytansinol 3-isobutyrate as a crude product. This crude product is dissolved in ethyl acetate, the solution is allowed to stand, and the resulting crystals are collected by filtration. The above procedure yields 44 mg of dechloromaytansinol 3-isobutyrate as white prisms.

m.p. 250°-252° C. (decompn.)

Mass spectrum (m/e): 600, 557, 539, 534, etc.

UV-spectrum ($\lambda_{max}^{MeOH}$)nm: 232.5, 241, 251, 277.5, 285.5

REFERENCE EXAMPLE 3

*Streptomyces flavotricini* IFO 12770 is used to inoculate a culture medium composed of 1% dextrin, 1% glucose, 1% glycerol, 0.5% peptone, 0.5% yeast extract, 0.5% meat extract, 0.3% NaCl and 0.5% calcium carbonate (pH 7.2), and is cultivated under shaking at 28° C. for 48 hours. To a 2 l portion of this culture is added 20 mg of Ansamytocin P-3 and the reaction is conducted under shaking at 28° C. for 48 hours. The reaction mixture is then extracted with ethyl acetate and the extract is filtered, washed with dilute hydrochloric acid, aqueous sodium hydrogen carbonate and water, dried and concentrated under reduced pressure. To the residue is added petroleum ether and the resultant precipitate is dissolved in a small amount of chloroform and purified by silica gel chromatography. The above precedure yields 12 mg white powders of PDM-3. m.p. 165°-168° C.

REFERENCE EXAMPLE 4

By the same procedure as Reference Example 3, dechloro-PDM-3 is obtained from dechloromaytansinol 3-isobutyrate. Rf=0.42 [solvent: chloroform-methanol=9:1, plate:silica gel glass plate (Merck 60 F$_{254}$)].

EXAMPLE 1

In 2.0 ml of anhydrous pyridine is dissolved 100.3 mg of PDM-3. To this solution, 142 μl of methanesulfonyl chloride is added. The mixture is stirred at room temperature for 2 hours. The pyridine is distilled off under reduced pressure, the residue is dissolved in dichloromethane and the solution is washed with 0.5 N—HCl, water and aqueous sodium hydrogen carbonate in that order and dried (Na$_2$SO$_4$). The solvent is then distilled off and the residue is chromatographed on silica gel (SiO$_2$, 12 g; solvent: ethyl acetate), the eluate being collected in 10-g fractions. Fractions 4 through 15 are pooled and the solvent is distilled off to obtain 74 mg of PDM-3-C$_{20}$-methanesulfonate. m.p. 230°–233° C. (decompn.), Mass spectrum (m/e): 698(M+), 637(M+—61).

EXAMPLE 2

In 5 ml of anhydrous pyridine is dissolved 94.3 mg of PDM-3. To this, 187.7 mg of p-toluenesulfonyl chloride is added. The mixture is stirred at room temperature for 8 hours and, then, allowed to stand at room temperature for 3 days. The pyridine is distilled off under reduced pressure and the residue is worked up as in Example 1. The residue is chromatographed on silica gel (SiO$_2$, 30 g; solvent, ethyl acetate), the eluate being collected in 10-g fractions. From fractions 7 through 20, 100.6 mg of PDM-3-C$_{20}$-p-toluenesulfonate is obtained. m.p. 172°–174° C. (decompn.), Mass spectrum (m/e): 713(M+-61).

EXAMPLE 3

As in Example 1, 101.2 mg of PDM-3 and 215.4 mg of p-chlorobenzenesulfonyl chloride are reacted in 2.0 ml of anhydrous pyridine at room temperature for 5 hours. The reaction mixture is worked up as in Example 1 and the resultant crude product is chromatographed on silica gel (SiO$_2$, 25 g; solvent, chloroform-methanol=50:1, v/v), the eluate being collected in 20-g fractions. From fractions 10 through 20, 115.1 mg of PDM-3-C$_{20}$-p-chlorobenzenesulfonate is obtained. m.p. 148°–152° C. (decompn.), Mass spectrum (m/e): 733(M+-61).

EXAMPLE 4

As in Example 1, 94.2 mg of PDM-3 and 218.7 mg of p-acetamidobenzenesulfonyl chloride are reacted in 2.2 ml of anhydrous pyridine at room temperature for 3 days. The pyridine is distilled off, the residue is dissolved in chloroform and the solution is washed and dried as in Example 1. The solvent is then distilled off and the residue is chromatographed on silica gel (SiO$_2$, 40 g; solvent, chloroform-methanol=50:1 to 40:1, v/v), the eluate being collected in 25-g fractions. Fractions 43 through 90 yield 107.5 mg of PDM-3-C$_{20}$-p-acetamidobenzenesulfonate. This product decomposes gradually at 180° to 200° C. Mass spectrum (m/e): 756(M+-61).

EXAMPLE 5

PDM-3 (101.2 mg) and 289.5 mg of p-trifluoroacetamidobenzenesulfonyl chloride are stirred in 2 ml of anhydrous pyridine at room temperature for 4 hours. The reaction mixture is worked up as in Example 1 to obtain PDM-3-C$_{20}$-p-trifluoroacetamidobenzenesulfonate as a crude product.

This crude product is dissolved in a mixture of 0.2 ml of ethylenediamine and 3 ml of pyridine and allowed to stand at room temperature overnight. The solvent is distilled off and the residue is chromatographed on silica gel (SiO$_2$, 45 g; solvent, chloroform-methanol=50:1, v/v), the eluate being collected in 25-g fractions. Fractions 20 through 29 are combined and the solvent is distilled off to yield 85.3 mg of PDM-3-C$_{20}$-p-aminobenzenesulfonate. m.p. 193°–195° C. (decompn.), Mass spectrum (m/e): 714 (M+-61).

EXAMPLE 6

As in Example 1, 22.5 mg of dechloro-PDM-3-C$_{20}$-methanesulfonate is obtained from 31.5 mg of dechloro-PDM-3, 50 μl of methanesulfonyl chloride and 1 ml of anhydrous pyridine. Mass spectrum (m/e): 603(M+-61).

EXAMPLE 7

As in Example 1, 95.8 mg of PDM-3 and 191 of α-toluenesulfonyl chloride (benzylsulfonyl chloride) are reacted in 2.0 ml of anhydrous pyridine at room temperature overnight. Then, the reaction mixture is worked up as in Example 1 and chromatographed on silica gel (SiO$_2$, 30 g; solvent: ethyl acetate), the eluate being collected in 10-g fractions to yield 97.0 mg of PDM-3-C$_{20}$-α-toluenesulfonate (PDM-3-C$_{20}$-benzylsulfonate). Mass spectrum (m/e): 713(M+-61).

EXAMPLE 8

PDM-3 (112.8 mg) is dissolved in 3 ml of dry pyridine. To this solution, 76 μl of ethanesulfonyl chloride is added dropwise with stirring and the mixture is stirred at room temperature for 3 hours. Then, 100 μl of ethanesulfonyl chloride is further added and the mixture is stirred at the same temperature for another 3 hours. Then, the pyridine is evaporated off under reduced pressure and the residue extracted with ethyl acetate. The extract is washed three times with aqueous NaCl solution and dried. The solvent is distilled off and the residue chromatographed on silica gel (SiO$_2$, 30 g; solvent: ethyl acetate-ethyl acetate saturated with water=5:1(v/v)), the eluate being collected in 10-g fractions. Fractions 9–16 are combined and split of the solvent and the residue is further separated by preparative thin layer chromatography (Merck, precoated silica gel plate, Art 5642; solvent: Ethyl acetate saturated with water) to give 25 mg of PDM-3-C$_{20}$-ethanesulfonate. Mass spectrum (m/e): 651(M+-61).

Experimental Data

Antitumor activity

Therapeutic tests were carried out in mice according to NCI-protocol 1,300, Cancer Chemother, Reports, Part 3, 1972, Vol.3, No.2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C %) |
|---|---|---|
| PDM-3-C$_{20}$-methenesulfonate | 200 | 246 |
| | 100 | 218 |
| | 50 | 189 |
| | 25 | 178 |
| | 12.5 | 195 |
| | 6.2 | 154 |

Antiprotozoal activity

Antiprotozoal activity of compound (I) was assayed with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The microorganism was incubated at 28° C.

for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC (µg/ml) Tetrahymena pyriformis W |
|---|---|
| PDM-3-$C_{20}$-p-toluenesulfonate | 1–2 |
| PDM-3-$C_{20}$-p-chlorobenzene-sulfonate | 2 |
| PDM-3-$C_{20}$-p-aminobenzene-sulfonate | 2–4 |

EXAMPLES OF PHARMACEUTICAL COMPOSITIONS

EXAMPLE A

| Composition for Injection | |
|---|---|
| (1) PDM-3-$C_{20}$-methanesulfonate | 100 mg |
| (2) Ethanol | 10 g |
| (3) Polysorbate 80 (tween 80) | 40 g |
| (4) Mannitol | 20 g |
| (5) Distilled water, a sufficient quantity to make | 1000 ml |

Preparation (1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

EXAMPLE B

| Composition for Injection | |
|---|---|
| (1) PDM-3-$C_{20}$-chlorobenzenesulfonate | 100 mg |
| (2) Ethanol | 5 g |
| (3) Polysorbate 80 (Tween 80) | 100 g |
| (4) Mannitol | 20 g |
| (5) Distilled water, a sufficient quantity to make | 1000 ml |

Preparation

By a similar procedure to that of Example A, an injectable solution of (I) is prepared.

What is claimed is:

1. A compound of the formula:

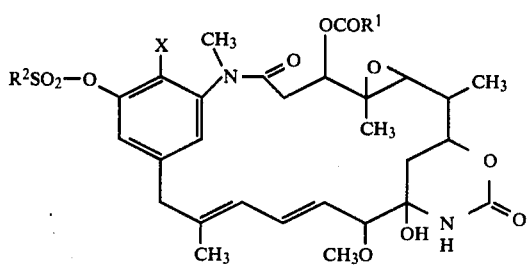

wherein X is H or Cl, $R^1$ is $C_{2-4}$ alkyl and $R^2$ is $C_{1-4}$ alkyl, phenyl or phenyl-$C_{1-3}$ alkyl, said phenyl or phenyl-$C_{1-3}$ alkyl being unsubstituted or substituted by $C_{1-4}$ alkyl, $C_{1-4}$ alkoxy, nitro, amino, mono or di-$C_{1-4}$ alkylamino, mono- or di-$C_{1-4}$ alkanoylamino, halogenated mono- or di-$C_{1-4}$ alkanoylamino, halogen or halogenated $C_{1-4}$ alkyl.

2. A compound according to claim 1, wherein $R^1$ is isopropyl.

3. A compound according to claim 1, wherein X is Cl.

4. A compound according to any of claims 1–3, wherein $R^2$ is $C_{1-4}$ alkyl.

5. A compound according to claim 4, wherein $R^2$ is methyl or ethyl.

6. A compound according to any of claims 1–3, wherein $R^2$ is phenyl or phenyl-$C_{1-3}$ alkyl, each of which is unsubstituted or substituted by $C_{1-4}$ alkyl, amino, $C_{1-4}$ alkanoylamino, halogenated $C_{1-4}$ alkanoylamino or halogen.

7. The compound according to claim 1, which is $C_{20}$-methanesulfonate of 20-demethoxy-20-hydroxymaytansinol 3-isobutyrate.

8. The compound according to claim 1, which is $C_{20}$-ethanesulfonate of 20-demethoxy-20-hydroxymaytansinol 3-isobutyrate.

9. The compound according to claim 1, which is $C_{20}$-p-toluenesulfonate of 20-demethoxy-20-hydroxymaytansinol 3-isobutyrate.

10. The compound according to claim 1, which is $C_{20}$-p-chlorobenzenesulfonate of 20-demethoxy-20-hydroxymaytansinol 3-isobutyrate.

11. The compound according to claim 1, which is $C_{20}$-p-aminobenzenesulfonate of 20-demethoxy-20-hydroxymaytansinol 3-isobutyrate.

12. A pharmaceutical composition suitable for inhibiting the growth of tumor cells and prolonging the survival time of a tumor-bearing warm-blooded animal, which comprises as an active ingredient an effective amount of a compound of the formula:

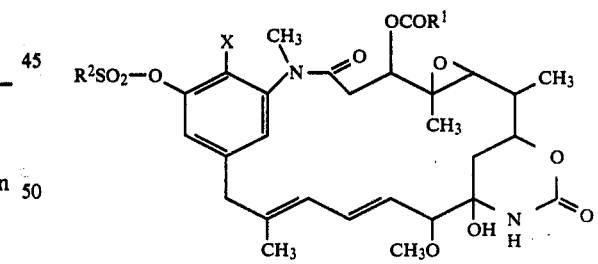

wherein X is H or Cl, $R^1$ is $C_{2-4}$ alkyl and $R^2$ is $C_{1-4}$ alkyl, phenyl or phenyl-$C_{1-3}$ alkyl, said phenyl or phenyl-$C_{1-3}$ alkyl being unsubstituted or substituted by $C_{1-4}$ alkyl, $C_{1-4}$ alkoxy, nitro, amino, mono- or di-$C_{1-4}$ alkylamino, mono- or di-$C_{1-4}$ alkanoylamino, halogenated mono- or di-$C_{1-4}$ alkanoylamino, halogen or halogenated $C_{1-4}$ alkyl, and a pharmaceutically acceptable carrier or diluent therefor.

13. A method for inhibiting the growth of tumor cells and prolonging the survival time of a tumor-bearing warm-blooded animal, which comprises administering to said animal an effective amount of a compound of the formula:

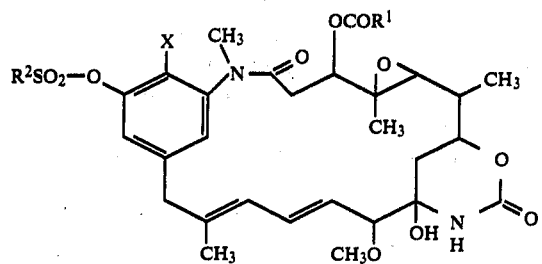
wherein X is H or Cl, $R^1$ is $C_{2-4}$ alkyl and $R^2$ is $C_{1-4}$ alkyl, phenyl or phenyl-$C_{1-3}$ alkyl, said phenyl or phenyl-$C_{1-3}$ alkyl being unsubstituted or substituted by $C_{1-4}$ alkyl, $C_{1-4}$ alkoxy, nitro, amino, mono- or di-$C_{1-4}$ alkylamino, mono- or di-$C_{1-4}$ alkanoylamino, halogenated mono- or di-$C_{1-4}$ alkanoylamino, halogen or halogenated $C_{1-4}$ alkyl.
* * * * *

UNITED STATES PATENT AND TRADEMARK OFFICE
CERTIFICATE OF CORRECTION

PATENT NO. : 4,264,596

DATED : April 28, 1981

INVENTOR(S) : Osamu MIYASHITA ET AL

It is certified that error appears in the above—identified patent and that said Letters Patent is hereby corrected as shown below:

In head-note, after the filing date, insert

--[30] July 31, 1979 [JP] Japan...........98010/1979.--

Signed and Sealed this

Twenty-eighth Day of July 1981

[SEAL]

Attest:

GERALD J. MOSSINGHOFF

Attesting Officer

Commissioner of Patents and Trademarks